United States Patent
Rakhit et al.

(10) Patent No.: US 6,919,328 B1
(45) Date of Patent: Jul. 19, 2005

(54) TRICYCLIC COMPOUNDS WITH NOS ACTIVITY

(75) Inventors: Suman Rakhit, Mississauga (CA); Jailall Ramnauth, Toronto (CA); Svetoslav Bratovanov, Toronto (CA); Shawn Maddaford, Mississauga (CA)

(73) Assignee: Neuraxon Inc., Toronto (CA)

( * ) Notice: Subject to any disclaimer, the term of this patent is extended or adjusted under 35 U.S.C. 154(b) by 161 days.

(21) Appl. No.: 10/265,624

(22) Filed: Oct. 8, 2002

Related U.S. Application Data

(60) Provisional application No. 60/327,317, filed on Oct. 9, 2001.

(51) Int. Cl.[7] .................. C07D 267/02; C07D 243/10; C07D 281/02; A61K 31/55

(52) U.S. Cl. .................. 514/211.04; 514/220; 540/488; 540/495

(58) Field of Search .............................. 514/211.04, 220; 540/488, 495

(56) References Cited

PUBLICATIONS

Ouyang et al. (Tetrahedron (1999), 55(10), 2827–2834).*
J. Ramnauth, S. Rakhit, S.P. Maddaford and S.S. Bratovanov, Canadian Society for Chemistry, 85th CSC Conference, Jun. 1–5, 2002, Vancouver, Abstract #995.

* cited by examiner

*Primary Examiner*—Bruck Kifle
(74) *Attorney, Agent, or Firm*—Bereskin & Parr

(57) ABSTRACT

The present invention provides novel tricyclic compounds, compositions comprising these compounds and methods of using these compounds as neuroprotectants. In particular, the compounds of the invention are useful for treating stroke.

15 Claims, No Drawings

TRICYCLIC COMPOUNDS WITH NOS ACTIVITY

The present invention claims the benefit of priority under 35 U.S.C. §119(e) from U.S. provisional patent application No. 60/327,317, filed on Oct. 9, 2001.

FIELD OF THE INVENTION

The present invention relates to novel tricyclic compounds having nitric oxide synthase (NOS) activity, to pharmaceutical and diagnostic compositions containing them and to their medical use, particularly as neuroprotectants.

BACKGROUND OF THE INVENTION

Nitric oxide (NO) has diverse roles both in normal and pathological processes including the regulation of blood pressure, in neurotransmission, and in the macrophage defense systems (Snyder, S. H., et al., *Scientific American*, May 1992, 68). NO is synthesized by three isoforms of nitric oxide synthase (NOS), two of which, one in endothelial cells (eNOS) and one in neuronal cells (nNOS), are constitutive, and the one, in macrophage cells, which is inducible (iNOS). These enzymes are homodimeric proteins that catalyzed a five-electron oxidation of L-arginine, yielding NO and citrulline. The role of NO produced by each of the NOS isoforms is quite unique. Overstimulation or overproduction of individual NOS isoforms plays a role in several disorders including septic shock, arthritis, diabetes, ischemia-reperfusion injury, pain and various neurodegenerative diseases (Kerwin, J. F. Jr., et al.,*J. Med. Chem.* 1995, 38, 4343). For example, the role of NO in cerebral ischemia can be protective or destructive depending on the stage of evolution of the ischemic process and on the cellular compartment producing NO (Dalkara, T., et al. *Brain Pathology*, 1994, 4, 49). While the NO produced by eNOS is likely beneficial by acting as a vasodilator to improve blood flow to the affected area (Huang, Z., et al. *J. Cereb. Blood Flow Metab.* 1996, 16, 981), NO produced by nNOS may contribute to the initial metabolic deterioration of the ischemic penumbra, resulting in larger infarcts (Hara, H., et al., *J. Cereb. Blood Flow Metab.* 1996, 16, 605). The metabolic derangement that occurs during ischemia and subsequent reperfusion results in the expression and release of several cytokines that activate iNOS in several cell types including some of the central nervous system. NO can be produced at cytotoxic levels by iNOS, and increased levels of iNOS contribute to progressive tissue damage in the penumbra, leading to larger infarcts (Parmentier, S., et al. Br. *J. Pharmacol.*, 1999, 127, 546). Inhibition of i-NOS has been shown to ameliorate cerebral ischemic damage in rats (*Am. J. Physiol.*, 268, R286 1995).

NO produced by I-NOS is also thought to play a role in diseases that involve systemic hypotension such as toxic shock and therapy with certain cytokines. It has been shown that cancer patients treated with cytokines such as interleukin 1 (IL-1), interleukin 2 (IL-2) or tumor necrosis factor (TNF) suffer cytokine-induced shock and hypotension due to NO produced from macrophages, i.e., inducible NOS (i-NOS) (*Chemical & Engineering News*, December 20, 33, 1993). i-NOS inhibitors can reverse this. Suppression of adjuvant induced arthritis by selective inhibition of i-NOS is reported in *Eur. J. Pharmacol.,* 273, p. 15–24 (1995).

n-NOS inhibition has also been shown to be effective in antinociception, as evidenced by activity in the late phase of the formalin-induced hindpaw licking and acetic acid-induced abdominal constriction assays (Br. *J. Pharmacol.*, 110, 219–224, 1993). Finally, opioid withdrawal in rodents has been reported to be reduced by n-NOS inhibition (see *Neuropsychopharmacol.*, 13, 269–293, 1995).

NOS inhibitors can be therapeutic in many disorders, but preservation of physiologically important nitric oxide synthase function requires the development of isoform-selective inhibitors.

SUMMARY OF THE INVENTION

It has been found that certain amino-substituted tricylic compounds show inhibition of the nNOS and iNOS isoforms of nitric oxide synthase.

The present invention therefore provides compounds of Formula I, and pharmaceutically acceptable salts, hydrates, solvates and prodrugs thereof:

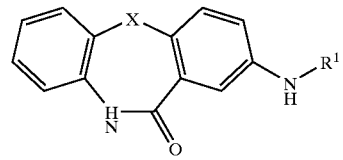

wherein
R$^1$ is selected from the group consisting of C(O)C$_{1-6}$alkyl, C(O)C$_{1-6}$alkenyl, C(O)Ar, C(O)NHAr, C(O)NHC$_{1-6}$alkyl, C(O)NHC(O)Ar, C(O)NHC(O)C$_{1-6}$alkyl C(O)NHC$_{1-6}$alkenyl, C(O)NH$_2$, C(S)NH$_2$, C(S)NHC$_{1-6}$alkyl, C(S)NHC$_{1-6}$alkyenyl, C(S)NHAr, C(S)NHC(O)Ar, C(S)NHC(O)C$_{1-6}$alkyl,

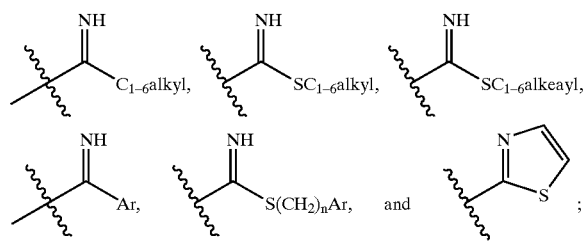

X is selected from the group consisting of O, NH, NC$_{1-4}$alkyl, and S; and n=1–4.

According to another aspect of the present invention, there is provided a pharmaceutical composition comprising a compound of the invention and a pharmaceutically acceptable carrier or diluent.

The compounds of the invention have been found to inhibit nNOS and iNOS. Accordingly, the present invention provides a method for inhibiting nNOS and/or iNOS comprising administering an effective amount of a compound of the invention to a cell or animal in need thereof. The invention also includes the use of a compound of the invention to inhibit nNOS and/or iNOS. Further, the invention includes a use of a compound of the invention to prepare a medicament to inhibit nNOS and/or iNOS.

The present invention further involves a method of treating and/or preventing a condition which benefits from the inhibition of nNOS and/or iNOS comprising administering an effective amount of a compound of the invention to a cell or animal in need thereof. The invention also includes the use of a compound of the invention to treat and/or prevent a condition which benefits from inhibition of nNOS and/or iNOS. Further, the present invention relates to a use of a compound of the invention to prepare a medicament to treat and/or prevent a condition which benefits from inhibition of nNOS and/or iNOS.

Inhibition of nNOS and/or iNOS may be beneficial for the treatment and/or prevention of a condition selected from the group consisting of migraine, inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer. Preferably the condition is stroke.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

I. Definitions

The term "$C_{1-4}$alkyl" as used herein means straight and/or branched chain alkyl radicals containing from one to four carbon atoms and includes methyl, ethyl, propyl, isopropyl, t-butyl and the like.

The term "$C_{1-6}$alkyl" as used herein means straight and/or branched chain alkyl radicals containing from one to six carbon atoms and includes methyl, ethyl, propyl, isopropyl, t-butyl, pentyl and the like.

The term "$C_{1-6}$alkenyl" as used herein means straight and/or ranched chain alkylene radicals containing from two to six carbon atoms and includes ethenyl, propenyl, 2-methyl-1-propenyl and the like.

The term "Ar" or "aryl" as used herein means unsubstituted or substituted mono- or bicyclic aromatic and heteroaromatic radicals containing from 6 to 10 carbon atoms of which 1–3 atoms may be a heteroatom selected from the group consisting of S, O and N, and includes furanyl, thienyl, pyrrolo, pyridyl, indolo, benzofuranyl, phenyl and naphthyl and the like. Optional substituents for Ar may be independently selected from 1–4 groups selected from $C_{1-4}$alkyl, $OC_{1-4}$alkyl, OH, $CF_3$, $OCF_3$, halo, $NO_2$, SH, $SC_{1-4}$alkyl, $NH_2$, $NHC_{1-4}$alkyl, $N(C_{1-4}$alkyl$)(C_{1-4}$alkyl$)$, CN, C(O)OH, C(O)O$C_{1-4}$alkyl, C(O)NH$C_{1-4}$alkyl, NHC(O) $C_{1-4}$alkyl, OC(O)$C_{1-4}$alkyl, SO$C_{1-4}$alkyl, $SO_2C_{1-4}$alkyl, $SO_2$NH$C_{1-4}$alkyl and $SO_2NH_2$.

The term "halo" as used herein means halogen and includes chloro, flouro, bromo, iodo and the like.

The term "pharmaceutically acceptable salt" means an acid addition salt or a basic addition salt which is suitable for or compatible with the treatment of patients.

The term "pharmaceutically acceptable acid addition salt" as used herein means any non-toxic organic or inorganic salt of any base compound of the invention, or any of its intermediates. Basic compounds of the invention that may form an acid addition salt include, for example, those where Ar is substituted with $NH_2$ or wherein $R^1$ comprises an imine, such as C(NH)$C_{1-6}$alkyl or C(NH)Ar. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the invention are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the invention, for laboratory use, or for subsequent conversion to a pharmaceutically acceptable acid addition salt.

The term "pharmaceutically acceptable basic addition salt" as used herein means any non-toxic organic or inorganic base addition salt of any acid compound of the invention, or any of its intermediates. Acidic compounds of the invention that may form a basic addition salt include, for example, those where Ar is substituted with C(O)OH. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art.

The term "solvate" as used herein means a compound of the invention wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "compound(s) of the invention" as used herein means a compound(s) of Formula I, and salts, hydrates, solvates and prodrugs thereof.

The term an "effective amount" or a "sufficient amount" of an agent as used herein is that amount sufficient to effect beneficial or desired results, including clinical results, and, as such, an "effective amount" depends upon the context in which it is being applied. For example, in the context of administering an agent that is an inhibitor of nNOS and/or iNOS, an effective amount of an agent is, for example, an amount sufficient to achieve such a reduction in nNOS and/or iNOS activity as compared to the response obtained without administration of the agent.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. "Palliating" a disease or disorder means that the extent and/or undesirable clinical manifestations of a disorder or a disease state are lessened and/or time course of the progression is slowed or lengthened, as compared to not treating the disorder.

To "inhibit" or "suppress" or "reduce" a function or activity, such as nNOS and/or iNOS activity, is to reduce the function or activity when compared to otherwise same conditions except for a condition or parameter of interest, or alternatively, as compared to another conditions.

The term "animal" as used herein includes all members of the animal kingdom including human. The animal is preferably a human.

The term "a cell" as used herein includes a plurality of cells. Administering a compound to a cell includes in vivo, ex vivo and in vitro treatment.

II. Compounds of the Invention

Novel compounds showing inhibition of nNOS and/or iNOS have been prepared. As such, the compounds of the invention are useful as neuroprotectants for treating conditions such as stroke.

Accordingly, the present invention provides compounds of Formula I, and pharmaceutically acceptable salts, hydrates, solvates and prodrugs thereof:

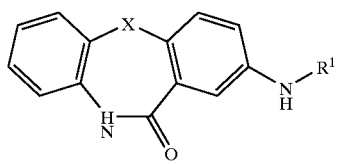

I wherein

R$^1$ is selected from the group consisting of C(O)C$_{1-6}$alkyl, C(O)C$_{1-6}$alkenyl, C(O)Ar, C(O)NHAr, C(O)NHC$_{1-6}$alkyl, C(O)NHC(O)Ar, C(O)NHC(O)C$_{1-6}$alkyl C(O)NHC$_{1-6}$alkenyl, C(O)NH$_2$, C(S)NH$_2$, C(S)NHC$_{1-6}$alkyl, C(S)NHC$_{1-6}$alkenyl, C(S)NHAr, C(S)NHC(O)Ar, C(S)NHC(O)C$_{1-6}$alkyl,

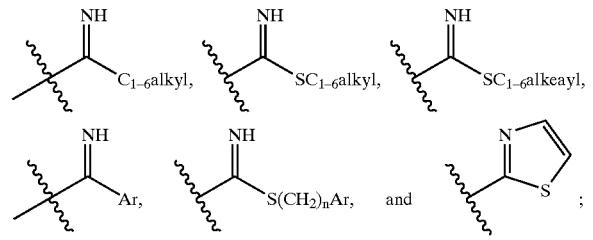

X is selected from the group consisting of O, NH, NC$_{1-4}$alkyl, and S; and n=1–4.

In its embodiments, the present invention includes compounds of Formula I wherein R$^1$ is selected from the group consisting of C(O)C$_{1-6}$alkyl, C(O)C$_{1-6}$alkenyl, C(O)Ar, C(O)NHAr, C(O)NHC$_{1-6}$alkyl, C(O)NHC(O)Ar, C(O)NHC(O)C$_{1-6}$alkyl, P(O)NHC$_{1-6}$alkenyl, C(O)NH$_2$, C(S)NH$_2$, C(S)NHC$_{1-6}$alkyl, C(S)NHC$_{1-6}$alkenyl, C(S)NHAr, C(S)NHC(O)Ar, C(S)NHC(O)C$_{1-6}$alkyl,

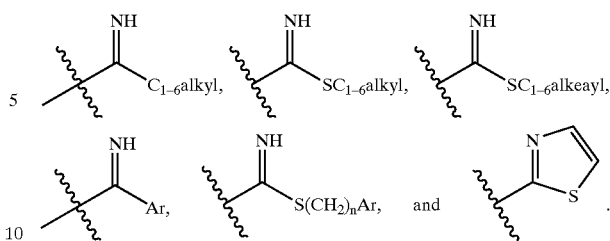

In preferred embodiments, R$^1$ in compounds of Formula I is selected from the group consisting of C(O)C$_{1-4}$alkyl, C(O)C$_{1-4}$alkenyl, C(O)Ar, C(Q)NHAr, C(O)NHC$_{1-4}$alkyl, C(O)NHC(O)Ar, C(O)NHC(O)C$_{1-4}$alkyl, C(O)NHC$_{1-4}$alkenyl, C(O)NH$_2$, C(S)NH$_2$, C(S)NHC$_{1-4}$alkyl, C(S)NHC$_{1-4}$alkenyl, C(S)NHAr, C(S)NHC(O)Ar, C(S)NHC(O)C$_{1-4}$alkyl,

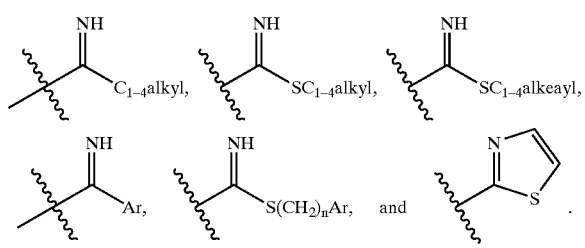

In more preferred embodiments, R$^1$ in compounds of Formula I is selected from the group consisting of C(O)CH$_3$, C(O)NHAr, C(O)NHCH$_3$, C(O)NHC(O)Ar, C(S)NHC$_{1-4}$alkyl, C(S)NHAr, C(S)NHC(O)Ar,

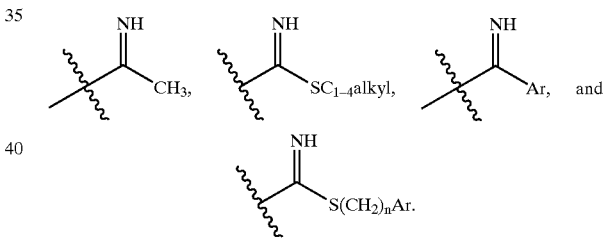

In the most preferred embodiments of the invention, R$^1$ in compounds of Formula I is selected from the groups consisting of

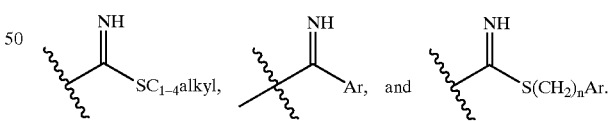

The term Ar in compounds of Formula I, as defined hereinabove, includes unsubstituted or substituted mono- or bicyclic aromatic and heteroaromatic radicals containing from 6 to 10 carbon atoms of which 1–3 atoms may be a heteroatom selected from the group consisting of S, O and N, and includes furanyl, thienyl, pyrrolo, pyridyl, indolo, benzofuranyl, phenyl and naphthyl and the like. In preferred embodiments of the present invention, Ar includes unsubstituted or substituted phenyl, naphthyl, pyridyl, thienyl, furanyl and indolo. Most preferably, Ar is selected from unsubstituted phenyl, naphthyl and thienyl. Optional substituents for aryl may be independently selected from 1–4 groups selected from C$_{1-4}$alkyl, OC$_{1-4}$alkyl, OH, CF$_3$, OCF$_3$, halo, NO$_2$, SH, SC$_{1-4}$alkyl, NH$_2$, NHC$_{1-4}$alkyl, N(C$_{1-4}$alkyl)(C$_{1-4}$alkyl), CN, C(O)OH, C(O)OC$_{1-4}$alkyl, C(O)NHC$_{1-4}$alkyl, NHC(O)C$_{1-4}$alkyl, OC(O)C$_{1-4}$alkyl, SOC$_{1-4}$alkyl, SO$_2$C$_{1-4}$alkyl, SO$_2$NHC$_{1-4}$alkyl and SO$_2$NH$_2$. Preferably Ar is optionally substituted with 1–2 groups independently selected from the group consisting of CH$_3$, OCH$_3$, OH, CF$_3$, OCF$_3$, halo, NO$_2$, NH$_2$, N(CH$_3$)$_2$, CN and C(O)OCH$_3$.

In further embodiments of the present in the invention, X in compounds of Formula I is selected from the group consisting of O, NH, NC$_{1-4}$alkyl, and S. In preferred embodiments, X is selected from the group consisting of O, NH, NCH$_3$ and S. In more preferred embodiments, X is selected from the group consisting of O and NH.

In other embodiments of the present invention, n is 1–4. In preferred embodiments n is 1–3.

In specific embodiments of the present invention, the compounds of Formula 1 include:
  N-(11-Oxo-10,11-dihydro-5H-dibenzo[b,e][1,4]diazepin-2-yl)-acetamide;
  1-Benzoyl-3-(11-oxo-10,11-dihydro-5H-dibenzo[b,e][1,4]diazepin-2-yl)-thiourea;
  (11-Oxo-10,11-dihydro-5H-dibenzo[b,e][1,4]diazepin-2-yl)-thiourea;
  2-Ethyl-1-(11-oxo-10,11-dihydro-5H-dibenzo[b,e][1,4]diazepin-2-yl)-isothiourea;
  N-(11-Oxo-10,11-dihydro-5H-dibenzo[b,e][1,4]diazepin-2-yl)-acetamidine hydrobromide;
  2-Naphthalen-2-ylmethyl-1-(11-oxo-10,11-dihydro-5H-dibenzo[b,e][1,4]diazepin-2-yl)-isothiourea;
  2-Benzyl-1-(11-oxo-10,11-dihydro-5H-dibenzo[b,e][1,4]diazepin-2-yl)-isothiourea;
  N-(11-Oxo-10,11-dihydro-dibenzo[b,f][1,4]oxazepin-2-yl)-acetamidine;
  1-Benzoyl-3-(11-oxo-10,11-dihydro-dibenzo[b,f][1,4]oxazepin-2-yl)-thiourea;
  (11-Oxo-10,11-dihydro-dibenzo[b,f][1,4]-oxazepin-2-yl)-thiourea;
  1-(11-Oxo-10,11-dihydro-dibenzo[b,f][1,4]oxazepin-2-yl)-3-phenyl-thiourea;
  N-(11-Oxo-10,11-dihydro-dibenzo[b,f][1,4]oxazepin-2-yl)-thiophene-2-carboxamidine hyrobromide;
  N-(11-Oxo-10,11-dihydro-5H-dibenzo[b,e][1,4]diazepin-2-yl)-thiophene-2-carboxamidine hydrobromide; and
  2-(Thiazol-2-ylamino)-5,10-dihydro-dibenzo[b,e][1,4]diazepin-11-one.

In more specific embodiments of the present invention, the compounds of Formula 1 include:
  1-Benzoyl-3-(11-oxo-10,11-dihydro-5H-dibenzo[b,e][1,4]diazepin-2-yl)-thiourea;
  2-Ethyl-1-(11-oxo-10,11-dihydro-5H-dibenzo[b,e][1,4]diazepin-2-yl)-isothiourea;
  2-Naphthalen-2-ylmethyl-1-(11-oxo-10,11-dihydro-5H-dibenzo[b,e][1,4]diazepin-2-yl)-isothiourea;
  2-Benzyl-1-(11-oxo-10,11-dihydro-5H-dibenzo[b,e][1,4]diazepin-2-yl)-isothiourea;
  1-Benzoyl-3-(11-oxo-10,11-dihydro-dibenzo[b,f][1,4]oxazepin-2-yl)-thiourea;
  (11-Oxo-10,11-dihydro-dibenzo[b,f][1,4]oxazepin-2-yl)-thiourea;
  N-(11-Oxo-10,11-dihydro-dibenzo[b,f][1,4]oxazepin-2-yl)-thiophene-2-carboxamidine hyrobromide; and
  N-(11-Oxo-10,11-dihydro-5H-dibenzo[b,e][1,4]diazepin-2-yl)-thiophene-2-carboxamidine hydrobromide.

In even more specific embodiments of the present invention, the compounds of Formula 1 include:
  2-Ethyl-1-(11-oxo-10,11-dihydro-5H-dibenzo[b,e][1,4]diazepin-2-yl)-isothiourea;
  2-Benzyl-1-(11-oxo-10,11-dihydro-5H-dibenzo[b,e][1,4]diazepin-2-yl)-isothiourea; and
  N-(11-Oxo-10,11-dihydro-5H-dibenzo[b,e][1,4]diazepin-2-yl)-thiophene-2-carboxamidine hydrobromide.

In the most specific embodiments of the present invention, the compound of Formula 1 is:
  2-Ethyl-1-(11-oxo-10,11-dihydro-5H-dibenzo[b,e][1,4]diazepin-2-yl)-isothiourea.

III. Methods of Preparing Compounds of the Invention

In accordance with another aspect of the present invention, the compounds of the invention can be prepared by processes analogous to those established in the art. Therefore, compounds of this invention may be prepared, for example, by the reaction sequences shown in Schemes 1–5.

When R$^1$ is selected from the group consisting of C(O)C$_{1-6}$alkyl, C(O)C$_{1-6}$alkylene and C(O)Ar, and X is as defined in Formula I, compounds of Formula I may be prepared, for example, as shown in Scheme 1. Therefore, tricyclic amines A, wherein X is as defined in Formula 1, may be reacted with an activated form of acids B, C or D under standard conditions. Activated forms of acids B, C and D may be prepared, for example by reaction under standard conditions with coupling reagents, such as dicyclohexylcarbodiimide/hydroxybenzotriazole (DCC/HOBT) or 1-ethyl-3-(3'-dimethylaminopropyl)carbodiimide hydrochloride (EDCl), or conversion to the acid chloride by reaction with, for example, oxalyl chloride or thionyl chloride. Alternatively, the anhydride of acids B, C and D may be coupled with amines A in the presence of a base.

Scheme 1

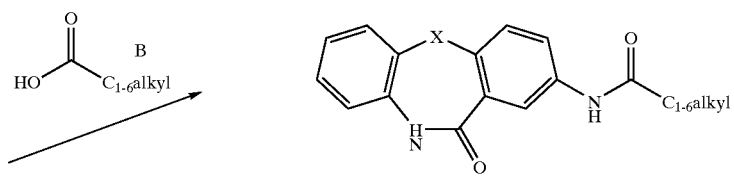

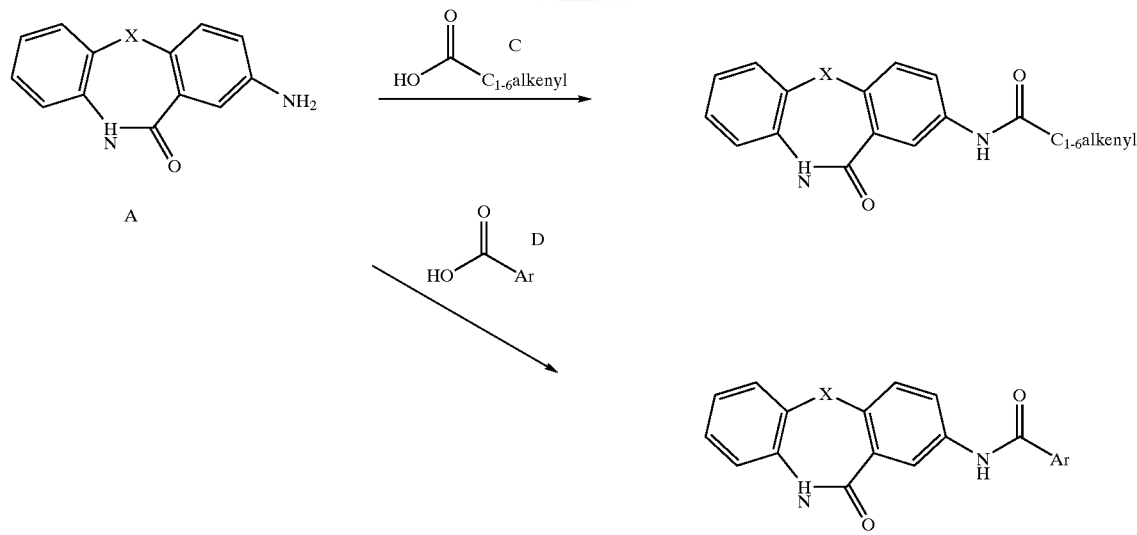

Compounds of Formula I, wherein $R^1$ is selected from the groups consisting of C(O)NHAr, C(O)NHC$_{1-6}$alkyl, C(O)NHC(O)Ar, C(O)NHC(O)C$_{1-6}$alkyl C(O)NHC$_{1-6}$alkenyl, C(S)NHC$_{1-6}$alkyl, C(S)NHC$_{1-6}$alkenyl, C(S)NHAr, C(S)NHC(O)Ar and C(S)NHC(O)C$_{1-6}$alkyl, and X is as defined in Formula I, may be prepared, for example, as shown in Scheme 2. Therefore, tricyclic amines of Formula A, wherein X is as defined in Formula I, may be reacted with isocyanates (Y=O) or isothiocyanates (Y=S) of the Formulae D–H in an inert solvent such as tetrahydrofuran (THF).

Scheme 2

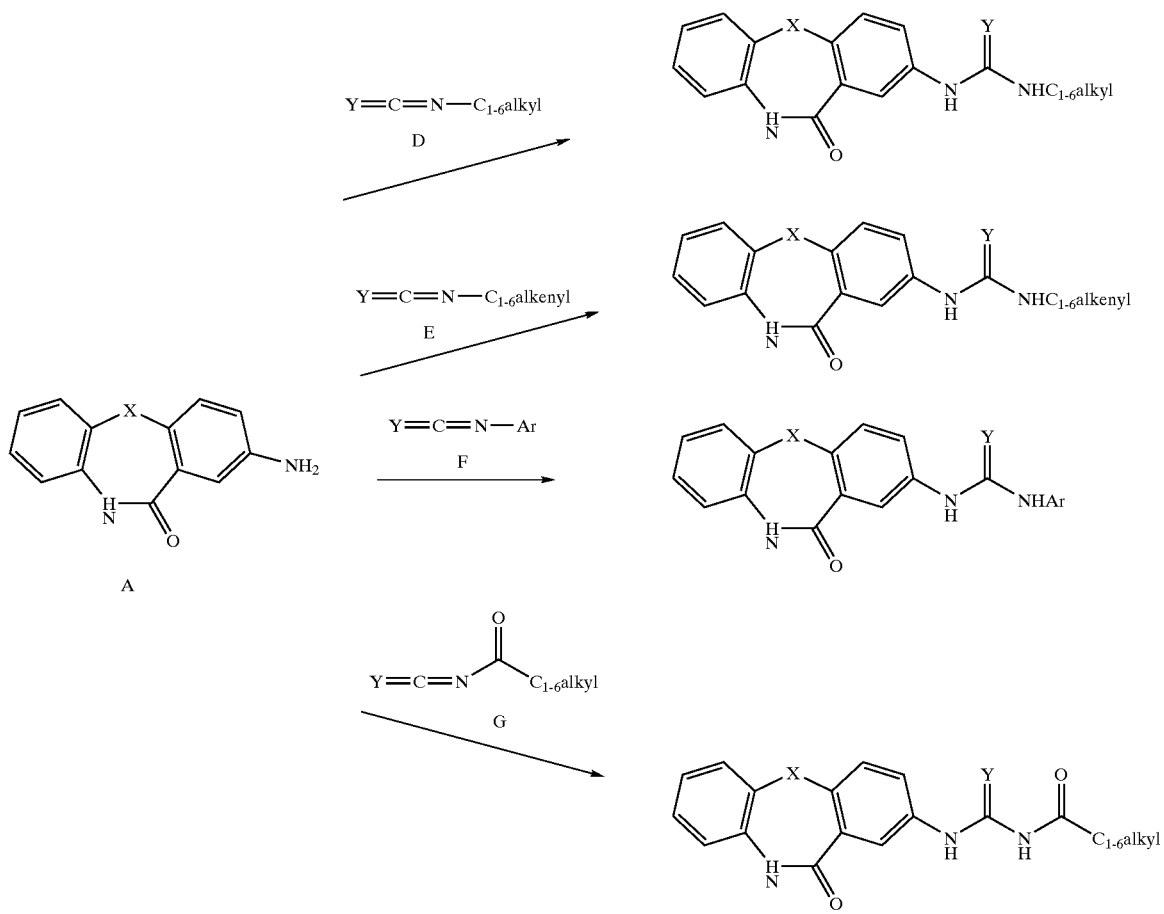

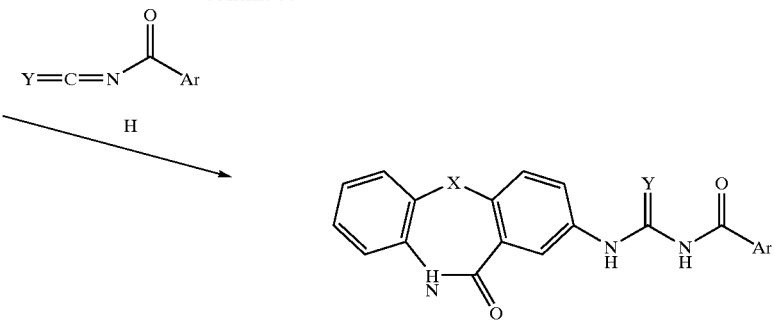

Compounds of Formula I, wherein $R^1$ is selected from $C(O)NH_2$ and $C(S)NH_2$, and X is as defined in Formula I, may be prepared by reacting compounds of Formula I, wherein $R^1$ is $C(Y)NHC(O)Ph$ and Y is O or S under standard hydrolysis conditions, for example using a base such as sodium hydroxide, as shown in Scheme 3.

Scheme 3

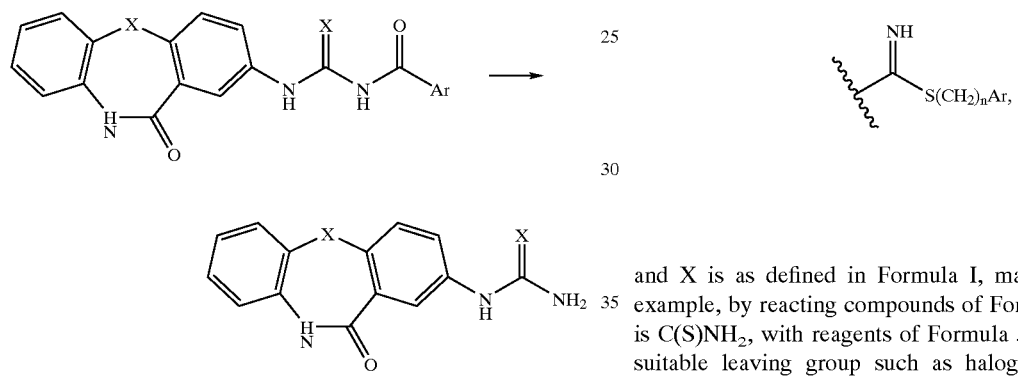

Compounds of Formula I, wherein $R^1$ is selected from

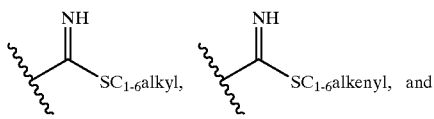

and X is as defined in Formula I, may be prepared, for example, by reacting compounds of Formula I, wherein $R^1$ is $C(S)NH_2$, with reagents of Formula J–L, wherein Z is a suitable leaving group such as halogen, under standard alkylation conditions, as shown in Scheme 4.

Scheme 4

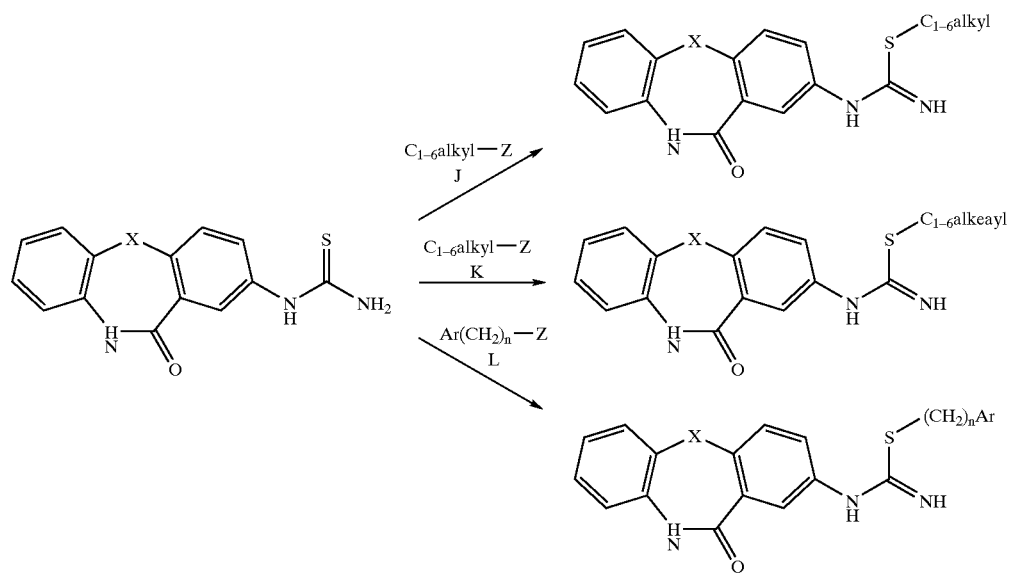

Compounds of Formula I, wherein $R^1$ is C(NH)Ar and C(NH)$C_{1-6}$alkyl, and X is as defined in Formula I, may be prepared, for example, as shown in Scheme 5. Therefore reagents of Formula A, may be reacted with reagents of Formula M or N, wherein Q may be, for example phenyl or naphthylmethyl, in an alcohol solvent such as ethanol to provide compounds of Formula I, wherein $R^1$ is C(NH)Ar and C(NH)$C_{1-6}$alkyl, respectively.

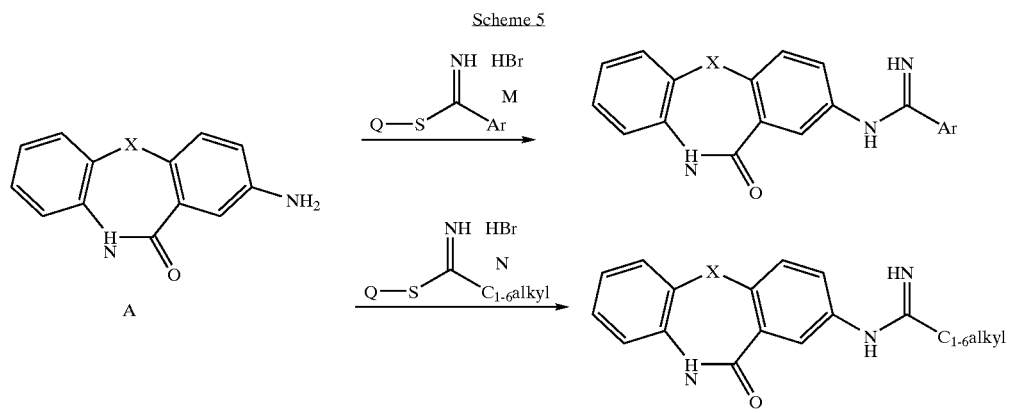

Scheme 5

Reagents of Formula M and N are either commercially available or may be prepared by reacting the corresponding cyano compounds with a thiol, Q—SH, wherein Q may be, for example phenyl or naphthylmethyl, followed by quenching with HBr, as shown in Scheme 6.

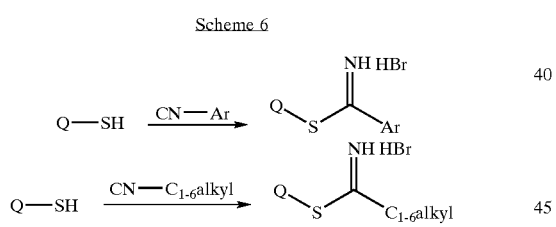

Scheme 6

Reagents of Formula A are well known in the art and may be prepared, for example, as shown in Scheme 7. In general, reagents of Formula P, may be coupled with reagents of Formual Q in either a one-step or two-step reaction sequence where the amine of reagents P is first coupled to the carboxyl of reagents Q, followed by ring closure to provide the nitro compounds of Formula S. Examples of the preparation of such compounds may be found in (Fu, J.-M. et al. U.S. Pat. No. 5,602,120, and references cited therein). Compounds of Formula S may then be reduced using standard procedures, for example using $SnCl_2$, to provide reagents of Formula A. Compounds of Formula S, wherein X=NH, may also be treated with a methylating reagent, such as methyliodide, in the presence of a base, to provide compounds of Formula S, wherein X=N$C_{1-4}$alkyl, which may then be reduced as described above to provide compounds of Formula A, wherein X=N$C_{1-4}$alkyl

Scheme 7

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 1991.

The formation of a desired compound salt is achieved using standard techniques. For example, the neutral compound is treated with an acid or base in a suitable solvent and the formed salt is isolated by filtration, extraction or any other suitable method.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of the invention may be conventional esters formed with available hydroxy, thiol, amino or carboxyl group. For example, when Ar is substituted with OH in a compound of the invention, it may be acylated using an activated acid in the presence of a base, and optionally, in inert solvent (e.g. an acid chloride in pyridine). Also, when Ar is substituted with C(O)OH in a compound of the invention, an ester may be formed by activation of the hydroxyl group of the acid and treatment with the appropriate alcohol in the presence of a base in an inert solvent. Some common esters which have been utilized as prodrugs are phenyl esters, aliphatic ($C_8$–$C_{24}$) esters, acyloxymethyl esters, carbamates and amino acid esters.

A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo (for example, compounds of Formula I wherein Ar is substituted with iodo), compound using standard palladium-catalyzed stannylation conditions, for example hexamethylditin in the presence of tetrakis(triphenylphosphine) palladium (0) in an inert solvent, such as dioxane, and at elevated temperatures, suitably 50–100° C.

IV. Uses

As hereinbefore mentioned, novel compounds having the general Formula I have been prepared. Accordingly, the present invention includes all uses of the compounds of the invention including their use in therapeutic methods and compositions for inhibiting nNOS and/or iNOS activity, their use in diagnostic assays and their use as research tools.

Compounds of the present invention have been found to be inhibitors of nNOS and/or iNOS isoforms. The present invention therefore provides a method for inhibiting nNOS and/or iNOS comprising administering an effective amount of a compound of the invention to a cell or animal in need thereof. The invention also includes the use of a compound of the invention to inhibit nNOS and/or iNOS. Further, the invention includes a use of a compound of the invention to prepare a medicament to inhibit nNOS and/or iNOS.

The present invention further involves a method of treating and/or preventing a condition which benefits from inhibition of nNOS and/or iNOS comprising administering an effective amount of a compound of the invention to a cell or animal in need thereof The invention also includes the use of a compound of the invention to treat and/or prevent a condition which benefits from inhibition of nNOS and/or iNOS. Further, the invention includes a use of a compound of the invention to prepare a medicament to treat and/or prevent a condition which benefits from inhibition of nNOS and/or iNOS.

As herein before mentioned, the NO produced by the nNOS isoform during cerebral ischemia may contribute to the initial metabolic deterioration of the ischemic penumbra, resulting in larger infarcts. Further, NO can be produced at cytotoxic levels by iNOS, and increased levels of iNOS contributes to progressive tissue damage in the penumbra, also leading to larger infarcts. The present invention therefore provides a method for treating stroke comprising administering an effective amount of a compound of the invention to a cell or an animal in need thereof. Further, there is provided a use of a compound of the invention to treat stroke as well as a use of a compound of the invention to prepare a medicament to treat stroke.

Other conditions that may benefit from inhibition of nNOS and/or iNOS include, but are not limited to migraine, inflammatory diseases (e.g., asthma), stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions (e.g., dependencies on drugs, alcohol and nicotine), emesis, epilepsy, anxiety, psychosis, head trauma, adult respiratory distress syndrome (ARDS), morphine induced tolerance and withdrawal symptoms, inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephropathy and cancer. Preferably the condition is stroke.

One skilled in the art can determine which compounds of the invention would have therapeutic utility, for example, as inhibitors of nNOS and/or iNOS. Compounds may be examined for their efficacy in preferentially inhibiting nNOS and/or iNOS using the methods described in Example 21. Further, the compounds of the invention may be tested in standard assays for neuroprotectants, in particular for stroke (see for example, Am. J. Physiol., 268, R286 1995). Accordingly, the methods, uses and compositions of the invention are meant to include only those compounds having the desired effect.

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent or carrier.

The compounds of the invention may be used in the form of the free base, in the form of salts, solvates and as hydrates. All forms are within the scope of the invention.

In accordance with the methods of the invention, the described compounds or salts or solvates thereof may be administered to a patient in a variety of forms depending on the selected route of administration, as will be understood by those skilled in the art. The compositions of the invention may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention thereof may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990—18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

The compounds of the invention may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds and/or compositions of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compounds of the invention may be administered initially in a suitable dosage that may be adjusted as required, depending on the clinical response.

The compounds of the invention can be used alone or in combination with other agents that have nNOS and/or iNOS activity or in combination with other types of treatment (which may or may not inhibit nNOS and/or iNOS) for the treatment and/or prevention of stroke or other disorders that benefit from nNOS and/or iNOS activity inhibition.

In addition to the above-mentioned therapeutic uses, the compounds of the invention are also useful in diagnostic assays, screening assays and as research tools.

In diagnostic assays the compounds of the invention may be useful in identifying or detecting nNOS and/or iNOS activity. In such an embodiment, the compounds of the invention may be radiolabelled (as hereinbefore described) and contacted with a population of cells. The presence of the radiolabel on the cells may indicate nNOS and/or iNOS activity.

In screening assays, the compounds of the invention may be used to identify other compounds that inhibit nNOS and/or iNOS. As research tools, the compounds of the invention may be used in enzyme assays and assays to study the localization of nNOS and/or iNOS activity. In such assays, the compounds may also be radiolabelled.

The following non-limiting examples are illustrative of the present invention:

EXAMPLES

Example 1

2-Chloro-5-nitro-benzoyl chloride

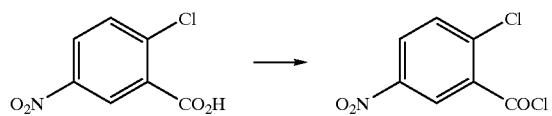

To a suspension of 2-chloro-5-nitro-benzoic acid (10 g, 49.6 mmol), oxalyl chloride was added dropwise (12.6 g, 2.0 equiv.). The resulting yellow solution was stirred at room temperature under argon overnight. The solvent was removed under vacuum to give a yellowish solid (10.8 g).

Example 2

2Chloro-N-(2-hydroxy-phenyl)-5-nitrobenzamide

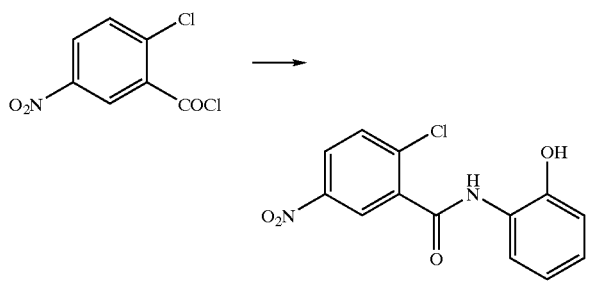

2-Chloro-5-nitro-benzoyl chloride in 60 mL of diethyl ether was added to an ice-cooled mixture of o-aminophenol (5.4 g) and sodium bicarbonate (8.3 g), water (36 mL) and ether (20 mL) over a period of 1 hour. The mixture was allowed to warm to room temperature and stirred overnight. The precipitate was filtered and washed sequentially with water (3×100 mL), 2N HCl (3×100 mL) and diethyl ether (3×50 mL). Yield 11.2 g (77%).

Example 3

2-Nitro-10H-dibenzo[b,f][1,4]oxazepin-11-one

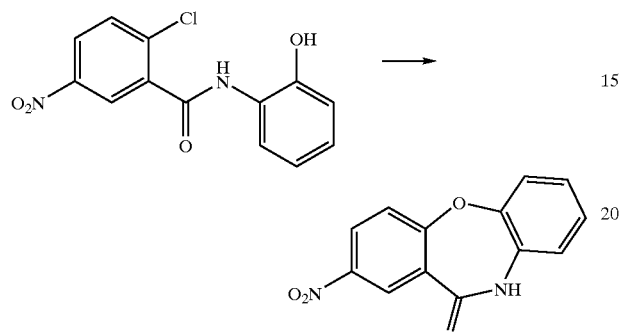

2-Chloro-N-(2-hydroxy-phenyl)-5-nitrobenzamide (10 g, 34.1 mmol) was added to a solution of sodium hydroxide (1.5 g, 37.6 mmol) in water (300 mL) and the resultant solution heated at 90° C. for 6 hr. The precipitate was filtered and washed with 4×100 mL of water. Yield 8.4 g (96%).

Example 4

2-Amino-10H-dibenzo[b,f][1,4]oxazepin-11-one

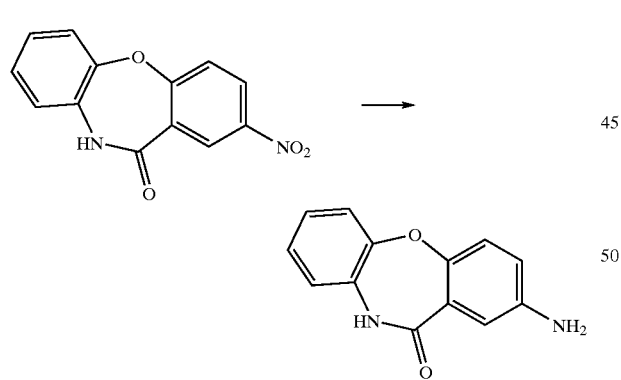

A mixture of 2-nitro-10H-dibenzo[b,f][1,4]oxazepin-11-one (Example 3, 2.0 g, 7.8 mmol) and SnCl$_2$ in 50 mL of denatured ethanol (85% ethanol, 15% wood alcohol) was stirred under reflux for 1 hr. The solvent was evaporated and the solid residue was washed with 200 mL of ethyl acetate. The ethyl acetate layer was washed with 1.0 N sodium hydroxide (2×100 mL) and water (2×100 mL), then dried over magnesium sulfate, filtered and evaporated to give an off white solid (yield 0.92 g, 52.3%).

Example 5

2-Nitro-5,10-dihydro-dibenzo[b,e][1,4]diazepin-11-one

2-Chloro-4-nitrobenzoic acid methylester (15 g, 69.6 mmol), 1,2-diaminobenzene (69.6 mmol) and triethylamine (9.7 mL, 69.7 mmol) were heated together at 90° C. in DMSO for 4 hr then to 120C for 1hr. After this time, the reaction was diluted with water (50 mL) and a reddish-brown precipitate formed. The solid was filtered off and washed with methanol (2×30 mL) to give the desired product (yield 7.6 g, 43%).

Example 6

2-Amino-5,10-hydrodo-benzo[b,e][1,4]diazepin-11-one

A mixture of 2-nitro-5,10-dihydro-dibenzo[b,e][1,4]diazepin-11-one (Example 5) and SnCl$_2$ in ethanol (10 mL) was stirred under reflux for 4 hr. The solvent was evaporated and the solid was extracted with 150 mL of ethyl acetate. The organic layer was washed with 1.0 N sodium hydroxide (2×100 mL), water (2×100 mL) and dried over sodium sulfate. The mixture was filtered and the solvent evaporated. The residue was purified by chromatography on silica gel using 80% ethyl acetate/20% hexanes and the eluant (yield 0.325 g, 74%).

Example 7

N-(11-Oxo-10,11-dihydro-5H-dibenzo[b,e][1,4]diazepin-2-yl)-acetamide

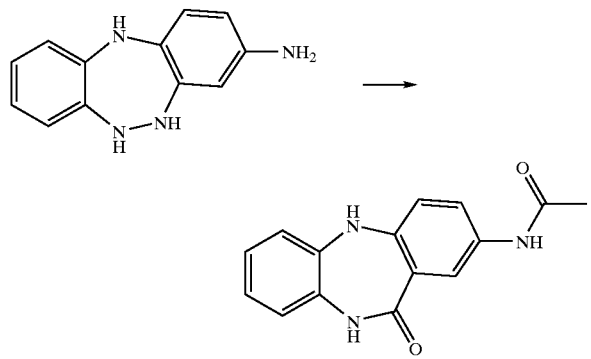

A solution of 2-amino-5,10-dihydro-dibenzo[b,e][1,4]diazepin-11-one (Example 6, 200 mg, 0.89 mmol) and triethylamine in tetrahydrofuran (10 mL) was cooled to 0° C. (ice-water bath). To this was added acetic anhydride (90.6 mg, 0.89 mmol) dropwise over a period of 10 minutes. The mixture was allowed to warm to room temperature and stirred overnight. The mixture was concentrated at reduced pressure and the residue was chromatographed on silica gel (80% ethyl acetate/20% hexanes then 100% ethyl acetate and finally 2% methanol/ethyl acetate) to give a yellow solid (120 mg, 50.4%). H1 NMR (DMSO d6) δ: 9.82 (s, 1H), 9.80 (s, 1H), 7.82–7.81 (d, 1H, J=4.0), 7.68 (s, 1H), 7.58–7.55 (m, 11H), 6.95–6.86 (m, 5H), 1.97 (s, 3H).

Example 8

1-Benzoyl-3-(11-oxo-10,11-dihydro-5H-dibenzo[b,e][1,4]diazepin-2-yl)-thiourea

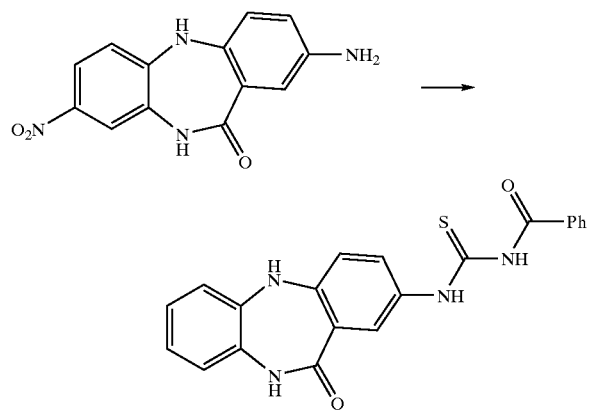

A stirred solution of 2-amino-5,10-dihydro-dibenzo[b,e][1,4]diazepin-11-one (Example 6, 0.5 g, 2.22 mmol) in 20 mL of THF was cooled to 0° C. (ice/water bath). Benzoyl isothiocyanate was added dropwise over a period of 10 min. The mixture was warmed to room temperature and stirred for 20 hr. The solvent was evaporated and the yellow solid washed with 50 mL of 1:1 ethyl acetate/hexanes solution (yield 0.736 g, 85%). H1 NMR (DMSO d6) δ: 12.43 (s, 1H), 11.53 (s, 1H), 9.92 (s, 1H), 8.00–7.95 (m, 3H), 7.06–6.96 (m, 6H), MS (ES): MH+ 389.1.

Example 9

(11-Oxo-10,11-dihydro-5H-dibenzo[b,e][1,4]diazepin-2-yl)-thiourea

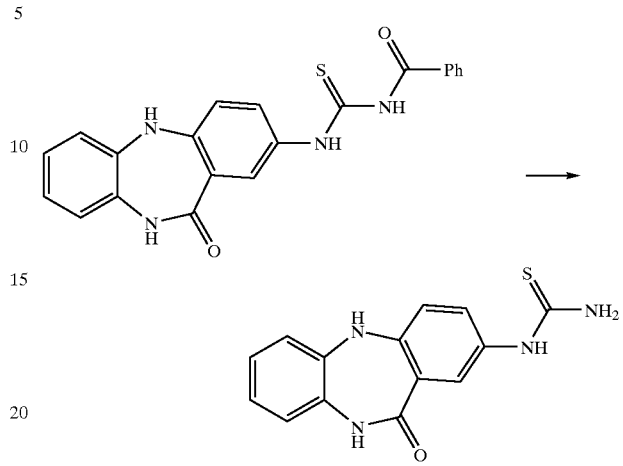

To a stirred solution of 1-benzoyl-3-(11-oxo-10,11-dihydro-5H-dibenzo[b,e][1,4]diazepin-2-yl)-thiourea (Example 8, 0.6 g, 1.54 mmol) in 10 mL of tetrahydrofuran was added 1.8 mL of 2.0 N aqueous sodium hydroxide. The mixture was heated to reflux for 3 hrs, diluted with water (10 mL) and extracted with ethyl acetate (3×100 mL). The combined organic fractions were dried with magnesium sulfate and concentrated under reduced pressure. The solid was washed with 1:1 ethyl acetate/hexanes (50 mL) to give a solid (yield 397 mg, 90.3%). H1 NMR (methanol d4) δ: 9.83 (s, 1H), 9.50 (s, 1H), 7.81 (s, 1H), 7.55–7.54 (d, 1H, J=1.9), 7.32–7.30 (m, 2H), 6.96–6.86 (m, 5H), 5.72 (s, 1H), MS (ES): MH+ 285.1.

Example 10

2-Ethyl-1-(11-oxo-10,11-dihydro-5H-dibenzo[b,e][1,4]diazepin-2-yl)-isothiourea

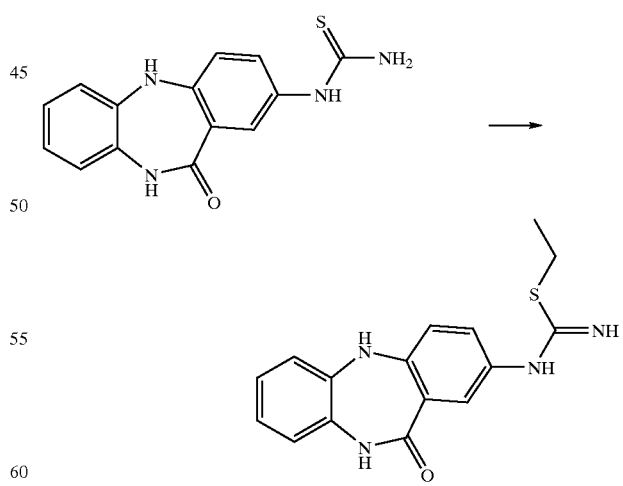

To a solution of (11-oxo-10,11-dihydro-5H-dibenzo[b,e][1,4]diazepin-2-yl)-thiourea (Example 9, 100 mg, 0.35 mmol) in DMSO was added ethyl iodide (28.2 μL, 0.35 mmol). The mixture was stirred at room temperature for 48 hr. DMSO was removed under vacuum and the residue was partitioned between ethyl acetate and saturated aqueous sodium bicarbonate. The organic layer was dried with magnesium sulfate, filtered and the solvent evaporated to give a yellow semi-solid which was chromatographed on silica gel (10% methanol/90% ethyl acetate) to give a yellow solid (109 mg, 55%). H1 NMR (DMSO d6) δ: 8.96 (s, 1H), 7.34 (s, 1H), 7.09–7.03 (m, 2H), 6.99–6.93 (m, 4H), 6.88–6.86 (m, 3H), 3.0–2.95 (q, 1H, J=7), 1.30–1.27 (t, 3H, J=7), MS (ES): MH$^+$ 313.2.

Example 11

N-(11-Oxo-10,11-dihydro-5H-dibenzo[b,e][1,4] diazeoin-2-yl)-acetamidine hydrobromide

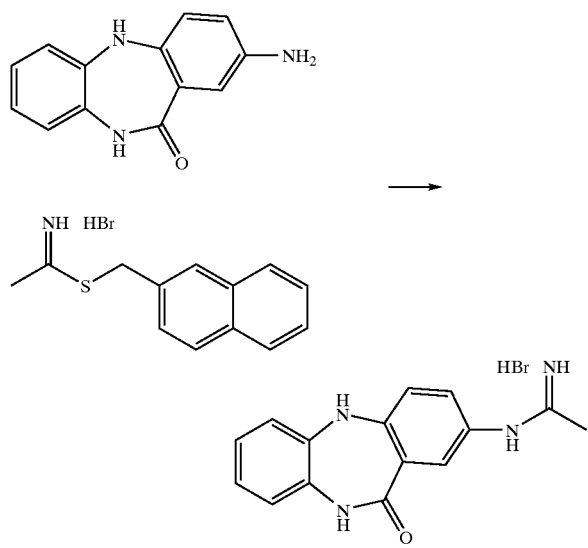

To an ice cold stirred solution of 2-amino-5,10-dihydro-dibenzo[b,e][1,4]diazepin-11-one (Example 6, 50.0 mg, 0.22 mmol) in ethanol (5 mL) was added thioacetimidic acid naphthalen-2-ylmethyl ester hydrobromide (65.8 mg, 0.22 mmol). After 2 hr. the solvent was evaporated and the residue was partitioned between 50 mL of ethyl acetate and 5 mL of water. The aqueous layer was separated and dried under vacuum (yield 71.0 mg, 93%). H1 NMR (D$_2$O) δ: 7.48–7.38 (m, 1H), 7.38–7.33 (m, 1H), 7.17–7.00 (m, 5H), 2.50 (s, 3H), MS (ES): MH$^+$ 267.3.

Example 12

2-Naphthalen-2-ylmethyl-1-(11-oxo-10,11-dihydro-5H-dibenzo[b,e][1,4]diazepin-2-yl)-isothiourea

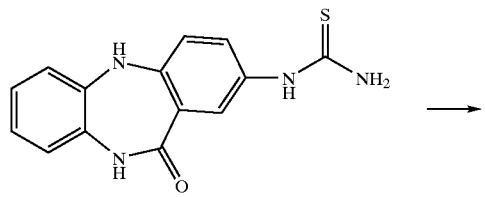

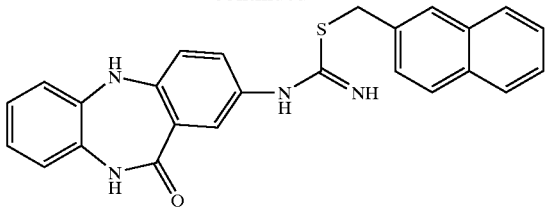

To a stirred solution of (11-oxo-10,11-dihydro-5H-dibenzo[b,e][1,4]diazepin-2-yl)-thiourea (Example 9, 50 mg, 0.18 mmol) in DMF (1 mL) was added 2-bromomethylnaphthalene (38.8 mg, 0.18 mmol) in one portion. The reaction mixture was stirred at room temperature for 1 hr then heated at 60° C. for 2 hrs. After this time, the solvent was removed in vacuo to leave an oily residue which was triturated with diethyl ether to give a yellow-brown solid. The solid was dissolved in 5 mL of tetrahydrofuran: 5 mL diethyl ether and treated with saturated sodium bicarbonate (10 mL). The organic layer was separated, dried over magnesium sulfate and evaporated to give a yellow oil. The product was purified by chromatography on silica gel (2% methanol: 98% dichloromethane). H1 NMR (acetone d6) δ: 8.81 (bs, 1H), 7.92–7.85 (m, 4H), 7.61 (bs, 1H), 7.50–7.39 (m, 4H), 7.09–6.91 (m, 7H), 5.81 (s, 2H).

Example 13

2-Benzyl-1-(11-oxo-10,11-dihydro-5H-dibenzo[b,e][1,4]diazepin-2-yl)-isothiourea

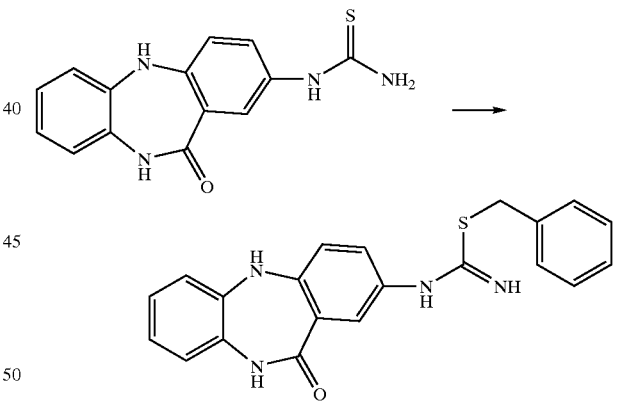

To a solution of (11-oxo-10,11-dihydro-5H-dibenzo[b,e][1,4]diazepin-2-yl)-thiourea (Example 9, 50 mg, 0.18 mmol) in DMF (1 mL) was added benzyl bromide (21 μL, 0.18 mmol). The solution was stirred at room temperature for 2 hr then heated at 60° C. for 1 hr. The solvent was removed under vacuo. The residue was dissolved in a mixture of tetrahydrofuran (5 mL) and diethyl ether (5 mL) and treated with 2 mL of saturated sodium bicarbonate solution. The organic layer was separated, dried over magnesium sulfate and evaporated to give an oily residue which was subjected to silica gel column chromatography (98% dichloromethane: 2% methanol). H1 NMR (acetone d6) δ: 8.91 (bs, 1H), 7.42–7.21 (m, 5H), 7.09–6.89 (m, 7H), 5.93 (bs, 1H), 4.31 (s, 2H).

Example 14

N-(11-Oxo-10,11-dihydro-dibenzo[b,f][1,4]oxazepin-2-yl)-acetamidine

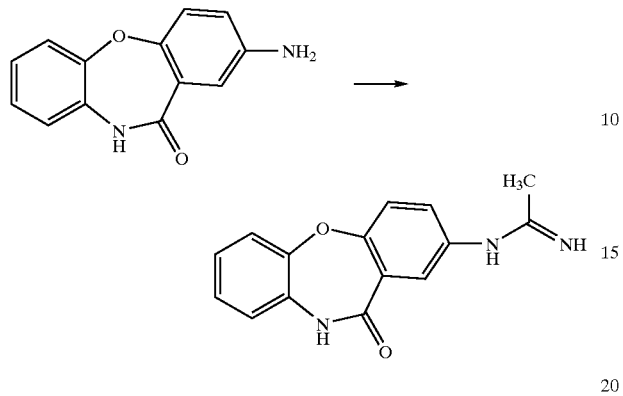

To a stirred solution of 2-amino-10H-dibenzo[b,f][1,4]oxazepin-11-one (Example 4, 50 mg, 0.22 mmol) in 4 mL of ethanol at 0° C. was added thioacetimidic acid naphthalen-2-ylmethyl ester hydrobromide (65 mg, 0.22 mmol). The reaction was warmed to room temperature overnight. The mixture was concentrated at reduced pressure and partitioned between water (5 mL) and ethyl acetate (25 mL). The aqueous layer was separated and evaporated under vacuum (yield 70 mg, 92%). H1 NMR (DMSO d6) δ: 11.15 (bs, 1H), 10.68 (s, 1H), 9.44 (bs, 1H), 8.56 (bs, 1H), 7.71–7.70 (m, 1H), 7.54–7.53 (m, 2H), 7.40–7.36 (m, 1H), 7.20–7.17 (m, 3H), 2.31 (s, 3H), MS (ES): MH+ 268.3.

Example 15

1-Benzoyl-3-(11-oxo-10,11-dihydro-dibenzo[b,f][1,4]oxazepin-2-yl)-thiourea

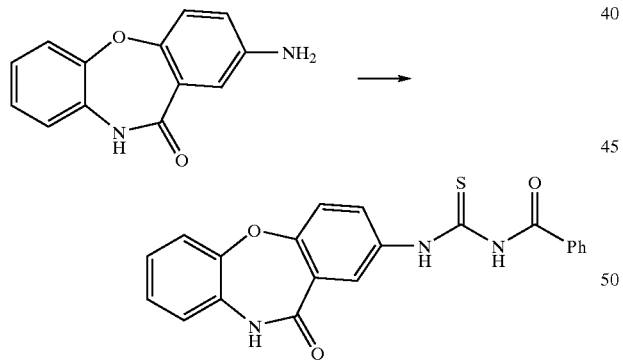

To a solution of 2-amino-10H-dibenzo[b,f][1,4]oxazepin-11one (Example 4, 0.3 9, 1.33 mmol) in 10 mL of tetrahydrofuran cooled to 0° C. was added dropwise benzoyllisothiocyanate (0.18 mL, 1.33 mmol). The reaction was allowed to warm to room temperature and stirred for 30 min. A white solid precipitated out. The solvent was evaporated and the solid was washed with 50 mL of a 1:1 ethyl acetate hexanes mixture (yield 0.402 9, 77%). H1 NMR (DMSO d6) δ: 12.43 (bs, 1H), 11.60 (bs, 1H), 10.59 (s, 1H), 8.04 (s, 1H), 7.96 (d, 2H, J=7.7), 7.83 (d, 1H, J=7.9), 7.65 (t, 1H, J=7.4), 7.53 (t, 2H, J=7.5), 7.39 (d, 1H, J=7.7), 7.34 (d, 1H, J=7.7), 7.18–7.15 (m, 3H).

Example 16

(11-Oxo-10,11-dihydro-dibenzo[b,f][1,4]oxazepin-2-yl)-thiourea

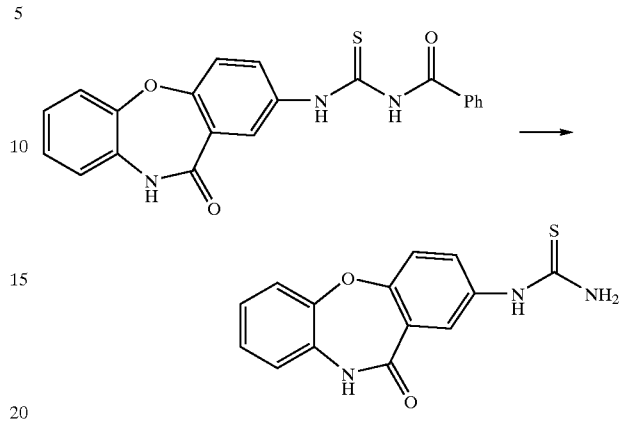

To a mixture of 1-benzoyl-3-(11-oxo-10,11-dihydro-dibenzo[b,f][1,4]oxazepin-2-yl)-thiourea (Example 15) in 15 mL of THF was added 1.0 mL of 2.0 N aqueous sodium hydroxide. The resulting solution was heated for 3 hr under reflux. The mixture was concentrated and the residue was triturated with 50 mL of a 10% THF:90% dichloromethane solution. The solid was filtered and washed with 30 mL of water (yield 201 mg, 78%). H1 NMR (CDCl$_3$) δ: 10.3 (bs, 1H), 7.74–7.61 (m, 3H), 7.28–7.15 (m, 3H), MS (ES): MH+ 286.1.

Example 17

1-(11-Oxo-10,11-dihydro-dibenzo[b,f][1,4]oxazegin-2-yl)-3-phenyl-thiourea

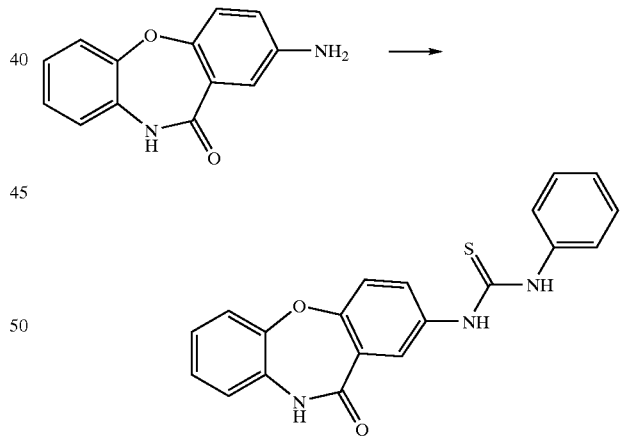

To a solution of 2-amino-10H-dibenzo[b,f][1,4]oxazepin-11-one (Example 4, 100 mg, 0.44 mmol) in 5 mL of THF was added phenylisothiocyanate (53 μL, 0.44 mmol). The solution was stirred at room temperature for 48 hr. The mixture was concentrated to give a yellow residue which was dissolved in 5 mL of a 5% methanol: 95% dichloromethane mixture. Upon standing, the product crystallized out of solution (40 mg, 25%, m.p. 199–200° C.). H1 NMR (DMSO d6) δ: 9.67 (bs, 1H), 9.00 (bs, 2H), 6.95–6.94 (m, 1H), 6.84–6.79 (m, 1H), 6.61–6.57 (m, 2H), 6.51–6.43 (m, 4H), 6.31–6.23 (m, 4H).

Example 18

N-(11-Oxo-10,11-dihydro-dibenzo[b,f][1,4]oxazepin-2-yl)-thiophene-2-carboxamidine hyrobromide

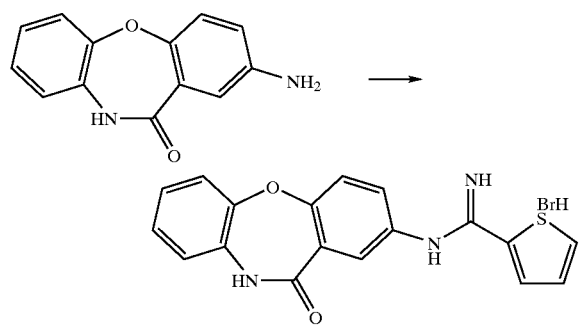

To a solution of 2-amino-10H-dibenzo[b,f][1,4]oxazepin-11-one (Example 4, 100 mg, 0.44 mmol) in methanol was added thiophene-2-carboximidothioic acid phenyl ester hydrobromide (146 mg, 0.48 mmol). The mixture was stirred at room temperature for 24 hr. The solvent was evaporated to give a yellow solid that was recrystalized from a mixture of ethanol and diethyl ether to give a yellow solid (yield 50 mg, 43%). H1 NMR (DMSO d6) δ: 11.38 (bs, 1H), 10.67 (s, 1H), 9.77 (bs, 1H), 8.95 (bs, 1H), 8.19–8.18 (m, 1H), 8.10 (s, 1H), 7.85 (s, 1H), 7.71–7.68 (m, 1H), 7.55–7.53 (m, 1H), 7.40–7.43 (m, 2H), 7.21–7.18 (m, 3H).

Example 19

N-(11-Oxo-10,11-dihydro-5H-dibenzo[b,e][1,4]diazepin-2-yl)-thiophene-2-carboxamidine hydrobromide

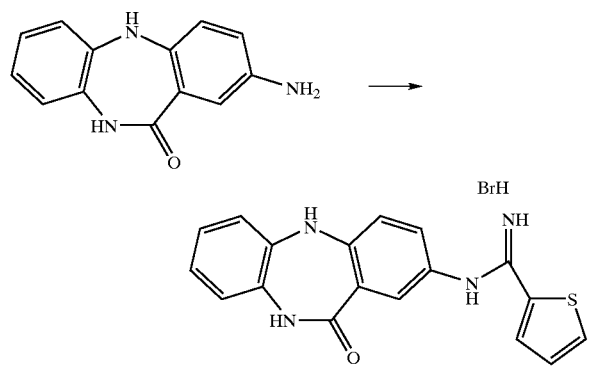

2-Amino-5,10-dihydro-dibenzo[b,e][1,4]diazepin-11-one (Example 6, 54 mg, 0.24 mmol) was dissolved in methanol (10 mL) and thiophene-2-carboximidothioic acid phenyl ester hydrobromide (79 mg, 0.26 mmol) added. The reaction was stirred at room temperature for 4 hr. The solvent was evaporated and the residue recrystallized from a mixture of methanol and ether to give a yellow solid. The solid was washed several times with ether (84 mg, 0.20, 84%).

Example 20

2-(Thiazol-2-ylamino)-5,10-dihydro-dibenzo[b,e][1,4]diazepin-11-one

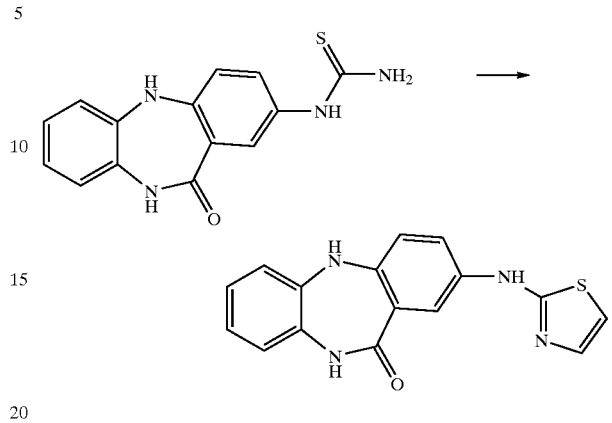

To a solution of (11-oxo-10,11-dihydro-5H-dibenzo[b,e][1,4]diazepin-2-yl)-thiourea (Example 9, 75 mg, 0.26 mmol) in ethanol (10 mL) was added chloroacetaldehyde (50% in water, 0.1 mL). The solution was refluxed for 5 hr and then concentrated under vacuum and poured into water (5 mL). The solution pH was adjusted to 9 with aqueous saturated sodium bicarbonate and then extracted with ethyl acetate. The organic phase was dried over magnesium sulfate and the solvent evaporated. The residue was recrystallized from ethanol/hexanes to give yellow solid (30 mg, 40%).

Example 21 nNOS and iNOS Enzyme Assay

The generation of nitric oxide by NOS was measured using the hemoglobin capture assay (*Proc. Natl. Acad. Sci., U.S.A.* 1990, 87, 714). As assay mixture for nNOS contained 10 mM L-arginine, 1.6 mM $CaCl_2$, 11.6 mg/mL calmoduline, 100 mM NADPH, 6.5 mM $BH_4$ and 3 mM oxyhemoglobin in 100 mM Hepes (pH 7.5). The reaction mixture for iNOS contained 10 mM of L-arginine, 100 mM NADPH, 6.5 mM $BH_4$ and 3 mM oxyhemoglobin in 100 mM Hepes (pH 7.5). All assays were in a final volume of 600 mL and were initiated with enzyme. Nitric oxide reacts with oxyhemoglobin to yield methehemoglobin which is detected at 401 nm ($e=19,700$ $M^{-1}cm^{-1}$) on a Perkin-Elmer Lamda 10 UV/vis spectrophotometer.

$IC_{50}$ and percent inhibition of NOS by the compounds of the invention was determined under initial velocity measurement condition with hemoglobin capture assay as described above using varying concentrations of the compounds of the invention. The results are shown in Tables 1 and 2.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

IC$_{50}$ (μM) f NOS by th C mp unds of the Inv ntion

| Example Number | nNOS | iNOS |
|---|---|---|
| 7 | 400 | 500 |
| 8 | 120 | 300 |
| 9 | 250 | 300 |
| 10 | 20 | 100 |
| 15 | 100 | 200 |
| 16 | 200 | 150 |
| 14 | 200 | 300 |
| 11 | 200 | 500 |

TABLE 2

Percent Inhibition of NOS by the Compounds of the Invention (at 100 μM)

| Example Number | nNOS | iNOS |
|---|---|---|
| 12 | 21 | 28 |
| 13 | 48 | 29 |
| 17 | 7 | 24 |
| 18 | 25 | 14 |
| 19 | 42 | 17 |

We claim:

1. A compound of Formula I, and pharmaceutically acceptable salts and solvates thereof:

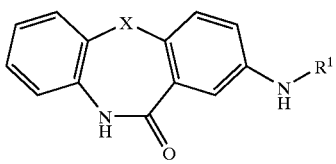

I wherein

R$^1$ is selected from the group consisting of C(O)C$_{1-6}$alkenyl, C(O)NHR$^2$, C(O)NHC$_{1-6}$alkyl, C(O)NHC(O)R$^2$, C(O)NHC(O)C$_{1-6}$alkyl, C(O)NHC$_{1-6}$alkenyl, C(O)NH$_2$, C(S)NH$_2$, C(S)NHC$_{1-6}$alkyl, C(S)NHC$_{1-6}$alkenyl, C(S)NHR$^2$, C(S)NHC(O)R$^2$, C(S)NHC(O)C$_{1-6}$alkyl,

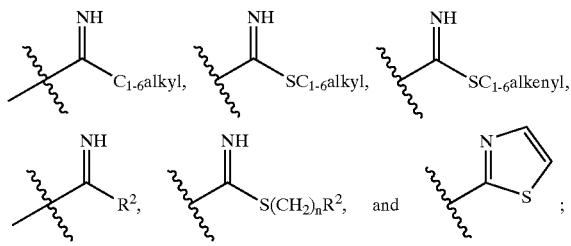

R$^2$ is selected from the group consisting of Ar and heteroaryl, wherein heteroaryl is a mono- or bicyclic heteroaromatic radical containing from 6 to 10 carbon atoms of which 1–3 atoms are a heteroatom selected from the group consisting of S, O and N and wherein both Ar and heteroaryl are either unsubstituted at substituted with 1–4 groups independently selected from C$_{1-4}$akyl, OC$_{1-4}$alkyl, OH, CF$_3$, OCF$_3$, halo, NO$_2$, SH, SC$_{1-4}$alkyl, NH$_2$, NHC$_{1-4}$alkyl, N(C$_{1-4}$alkyl)(C$_{1-4}$alkyl), CN, C(O)OH, C(O)OC$_{1-4}$alkyl, C(O)NHC$_{1-4}$alkyl, NHC(O)C$_{1-4}$alkyl, OC(O)C$_{1-4}$alkyl, SOC$_{1-4}$alkyl, SO$_2$C$_{1-4}$alkyl, SO$_2$NHC$_{1-4}$alkyl and SO$_2$NH$_2$;

X is selected from the group consisting of O, NH, NC$_{1-6}$alkyl, and S; and n=1–4.

2. The compound according to claim 1, wherein R$^1$ is selected from the group consisting of C(O)C$_{1-4}$alkenyl, C(O)NHR$^2$, C(O)NHC$_{1-6}$alkyl, C(O)NHC(O)R$^2$, C(O)NHC(O)C$_{1-4}$alkyl, C(O)NHC$_{1-4}$alkenyl, C(O)NH$_2$, C(S)NH$_2$, C(S)NHC$_{1-4}$alkyl, C(S)NHC$_{1-4}$alkenyl, C(S)NHR$^2$, C(S)NHC(O)$^2$, C(S)NHC(O)C$_{1-4}$alkyl,

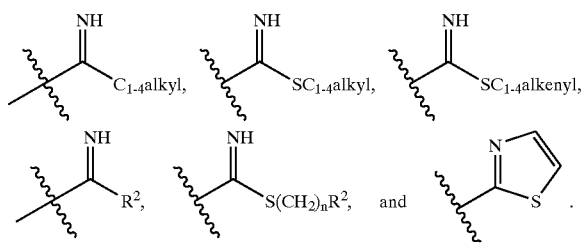

3. The compound according to claim 2, wherein R$^1$ is selected from the group consisting of C(O))NHR$^2$, C(O)NHCH$_3$, C(O)NHC(O)R$^2$, C(S)NHC$_{1-4}$alkyl, C(S)NHR$^2$, C(S)NMC(O)R$^2$,

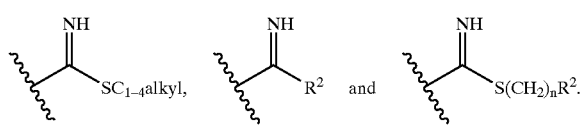

4. The compound of claim 3, wherein R$^1$ is selected from the group consisting of

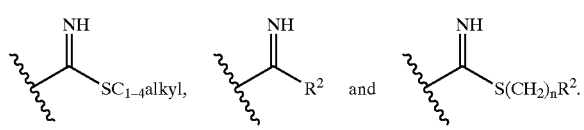

5. The compound according to claim 1, wherein R$^2$ is selected from the group consisting of unsubstituted or substituted phenyl, naphthyl, pyridyl, thienyl, furanyl, indolo.

6. The compound according to claim 5, wherein R$^2$ is selected from group consisting of unsubstituted phenyl, naphthyl and thienyl.

7. The compound according to claim 1, wherein R$^2$ is unsubstituted or substituted with 1–2 groups independently selected from the group consisting of CH$_3$, OCH$_3$, OH, CF$_3$, OCF$_3$, halo, NO$_2$, NH$_2$, N(CH$_3$)$_2$, CN and C(O)OCH$_3$.

8. The compound according to claim 1, wherein X is selected from the group consisting of O, NH, NCH$_3$ and S.

9. The compound according to claim 8, wherein X is selected from the group consisting of O and NH.

10. The compound according to claim 1, wherein n is 1–3.

11. The compound according to claim 1, selected from the group consisting of:

1-Benzoyl-3-(11-oxo-10,11-dihydro-5H-dibenzo[b,e][1,4]diazepin-2-yl)-thiourea;

(11-Oxo-10,11-dihydro-5H-dibenzo[b,e][1,4]diazepin-2-yl)-thiourea;

2-Ethyl-1-(11-oxo10,11-dihydro-5H-dibenzo[b,e][1,4]diazepin-2-yl)-isothiourea;

N-(11-Oxo-10,11-dihydro-5H-dibenzo[b,e][1,4]diazepin-2-yl)-acetamidine hydrobromide;

2-Naphthalen-2-ylmethyl-1-(11oxo-10,11-dihydro-5H-dibenzo[b,e][1,4]diazepin-2-yl)-isothiourea;

2-Benzyl-1-(11-oxo-10,11-dihydro-5H-dibenzo[b,e][1,4]diazepin-2-yl)-isothiourea;

N-(11-Oxo-10,11-dihydro-dibenzo[b,f][1,4]oxazepin-2-yl)-acetamidine;

1-Benzoyl-3-(11-oxo-10,11-dihydro-dibenzo[b,f][1,4]oxazepin-2-yl)-thiourea;

(11-Oxo-10,11-dihydro-dibenzo[b,f][1,4]oxazepin-2-yl)-thiourea;

1-(11-Oxo-10,11-dihydro-dibenzo[b,f][1,4]oxazepin-2-yl)-3-phenyl-thiourea;

N-(11-Oxo-10,11-dihydro-benzo[b,f][1,4]oxazepin-2-yl)-thiophene-2-carboxamidine hyrobromide;

N-(11-Oxo-10,11-dihydro-5H-dibenzo[b,e][1,4]diazepin-2-yl)-thiophene-2-carboxamidine hydrobromide; and 2-(Thiazol-2-ylamino)-5,10-dihydro-dibenzo[b,e][1,4]diazepin-11-one.

12. The compound according to claim 11, selected from the group consisting of:

1-Benzoyl-3-(11-oxo-10,11-dihydro-5H-dibenzo[b,e][1,4]diazepin-2-yl)-thiourea;

2-Ethyl-1-(11-oxo-10,11-dihydro-5H-dibenzo[b,e][1,4]diazepin-2-yl)-isothiourea;

2-Naphthalen-2-ylmethy-1-(11-oxo-10,11-dihydro-5H-dibenzo[b,e][1,4]diazepin-2-yl)-isothiourea;

2-Benzyl-1-(11-oxo-10,11-dihydro-5H-dibenzo[b,e][1,4]diazepin-2-yl)-isothiourea;

1-Benzoyl-3-(11-oxo-10,11-dihydro-dibenzo[b,f][1,4]oxazepin-2-yl)-thiourea;

(11-Oxo-10,11-dihydro-dibenzo[b,f][1,4]oxazepin-2-yl)-thiourea;

N-(11-Oxo-10,11-dihydro-dibenzo[b,f][1,4]oxazepin-2-yl)-thiophene-2-carboxamidine hyrobromide; and N-(11-Oxo-10,11-dihydro-5H-dibenzo[b,e][1,4]diazepin-2-yl)-thiophene-2-carboxamidine hydrobromide.

13. The compound according to claim 12 selected from the group consisting of:

2-Ethyl-1-(11-oxo-10,11-dihydro-5H-dibenzo[b,e][1,4]diazepin-2-yl)-isothiourea;

2-Benzyl-1-(11-oxo-10,11-dihydro-5H-dibenzo[b,e][1,4]diazepin-2-yl)-isothiourea; and N-(11-Oxo-10,11-dihydro-5H-dibenzo[b,e][1,4]diazepin-2-yl)-thiophene-2-carboxamidine hydrobromide.

14. The compound according to claim 13, that is:

2-Ethyl-1-(11-oxo-10,11-dihydro-5H-dibenzo[b,e][1,4]diazepin-2-yl)-isothiourea.

15. A pharmaceutical composition comprising a compound according to claim 1 and a pharmaceutically acceptable carrier.

* * * * *